United States Patent [19]
Syska et al.

[11] Patent Number: 6,159,199
[45] Date of Patent: Dec. 12, 2000

[54] DEVICE FOR THE MANIPULATION OF CYTOTECHNICAL INSTRUMENTS

[75] Inventors: Peter Syska, Norderstedt; Bernd Krueger, Tangstedt, both of Germany

[73] Assignee: Eppendorf-Netheler-Hinz GmbH, Hamburg, Germany

[21] Appl. No.: 09/150,437

[22] Filed: Sep. 9, 1998

[30] Foreign Application Priority Data

Sep. 13, 1997 [DE] Germany ............ 197 40 324

[51] Int. Cl.⁷ ............................................ A61B 17/00
[52] U.S. Cl. ............................. 606/1; 422/99; 901/50
[58] Field of Search ............... 606/1, 130; 414/1; 395/80, 82, 83; 422/50, 99; 901/50

[56] References Cited

U.S. PATENT DOCUMENTS

| | | |
|---|---|---|
| 5,762,458 | 6/1998 | Wang et al. ............... 414/1 |
| 5,800,423 | 9/1998 | Jensen ..................... 606/1 |

FOREIGN PATENT DOCUMENTS 0 577 084   1/1994   European Pat. Off. .

*Primary Examiner*—Linda C. M. Dvorak
*Assistant Examiner*—Bryan K. Yarnell
*Attorney, Agent, or Firm*—Brown & Wood, LLP

[57] ABSTRACT

A device for handling instruments used in technical cytological examinations has a holder base with at least two separate and moveable holders each carrying one instrument and each being coupled with a drive for switching the holders between two defined positions, one of which is a working position and the other is a rest position. In the working position, the distal end of the instrument located in the holder is aligned during a technical cytological intervention in the region of cellular material which is to be treated. In the rest position, the instrument held in the holder is kept at a safe distance from the cellular material which is to be treated. The drives are coupled with each other so that, when activated, they switch the holders between their rest and working position, respectively.

6 Claims, 2 Drawing Sheets

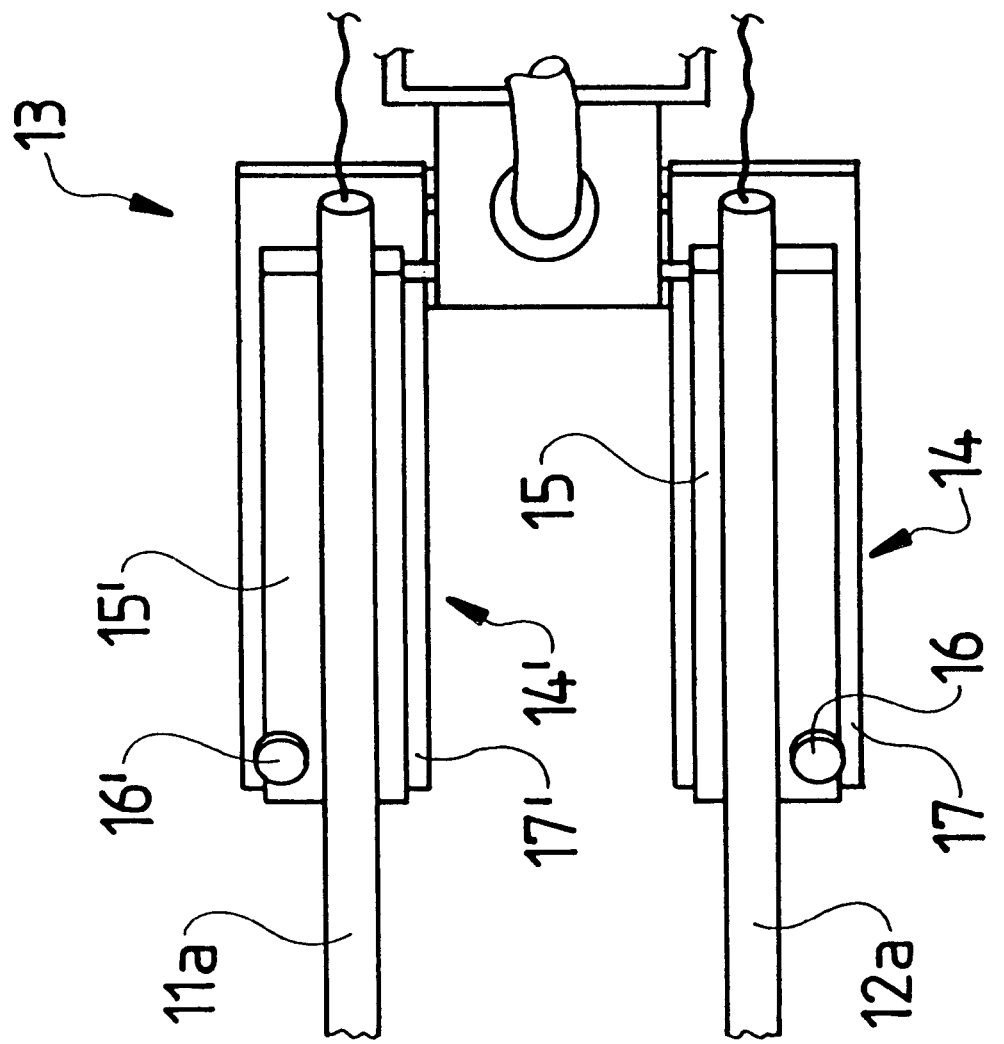

DEVICE FOR THE MANIPULATION OF CYTOTECHNICAL INSTRUMENTS

FIELD OF THE INVENTION

This invention concerns a device for handling instruments used in technical cytological examinations, comprising a holder base that makes available at least two separate and moveable holders each of which contains one instrument and each of which is coupled to a drive by which the holders can be switched between two defined positions, one of which is a working position in which the instrument located in the holder is aligned with its free end during a technical cytological intervention in the region of the cellular material which is to be treated, and the other of which is a resting position in which the instrument held in the holder is kept at a safe distance from the cellular material to be treated.

BACKGROUND OF THE INVENTION

Devices of this general type are used during technical cytological interventions. By the concept "cytological technology," we mean the investigation and handling of individual animal, plant or bacteria cells or of cell cultures, or even of organized cellular structures, in the broad sense. An important practical use is, for example, in pre-natal, pre-implantation diagnosis during which cell samples are taken from embryos and then investigated for the presence of possible genetically caused diseases or in order to determine the gender of the embryo.

The instruments used during technical cytological interventions will be called technical cytological instruments within the framework of this patent application. In this context, these may be especially capillary tubes or pipettes, but also precision pricking or cutting instruments or electrodes, depending upon the desired practical use.

A typical technical cytological intervention is for instance as follows:

The cellular material that is to be treated—an embryo, for example—is placed in a drop of culture medium in a Petrie dish and coated over with a layer of oil. The cellular material is then bonded, for example, with a retaining capillary tube and on the tube opening by vacuum. Under microscopic examination an acid culture solution is applied to the cell wall of the embryo using an additional capillary tube (the etching capillary) and in this way a hole is etched in the wall. The etching capillary tube is then removed and a blastomere is removed from the embryo using an additional capillary tube (a biopsy capillary) through the hole which was made in the wall of the cell.

Technical cytological interventions are usually performed under optical inspection using a powerful magnifying microscope during which the operator has only a very restricted field of vision available to him. One problem that arises during the exchange of instruments—for example, the exchange of the etching and biopsy capillaries mentioned above—is that, depending on the circumstances, the instrument which one wishes to use next may not be located in the user's field of vision, and the process of re-locating and adjusting its free end in the focal plane of the user's field of vision is relatively time consuming one.

Generally, such devices are thus equipped, for example, with a holder base which provides a separate, moveable holder for each instrument. Each of the holders is coupled to a drive which can shift it from a resting to a working position. Before beginning an intervention, the holder base which is outfitted with the instruments is macroscopically pre-adjusted, and then each of its holders is precisely adjusted by means of set screws, for example, until in the working position the free ends of the instruments mounted in the holders are mapped into the field of vision of the microscope. In this way it is made certain that—while a specific holder is being shifted into the working position— the free end of the instrument held in the selected holder is automatically placed into the operator's field of vision and thereby in direct proximity to the cellular material to be treated, and that it does not have to be re-adjusted by the operator each time in a time-consuming process.

In the working position, the free end of an instrument that is directly engaged in the examination is located on the same plane as, and in direct proximity to, the cell to be treated. Thereafter, the free end of a hollow needle or of any other instrument, for example, can be brought into the desired position on the surface of the cell by positioning the Petrie dish or even the holder base.

As noted above, the holders can be switched between the working position, which has been explained above, and a resting position. The resting position now especially needs to be selected and engaged when the samples of cellular materials that have to be processed are being exchanged. In the majority of cases several such samples are arranged either in a row or else even randomly placed on a Petrie dish. When changing over between two samples, the Petrie dish is positioned until the desired sample has been aligned in the field of vision of the microscope. While this is being done, one needs to make sure that none of the instruments (or of the holders containing the instruments) is set in the working position, i.e., with its free end located on the same level as the cellular material, because this would create the danger that the instrument might damage the cellular material during the largely uncontrolled movement of the Petrie dish.

For this reason, the invention provides for the drives being able to shift the holders not only into a defined working position, but also being able to shift the holders out of this position and into a defined resting position. In the resting position the instruments are aligned in such a way as to guarantee that a sufficiently safe distance to the biological material on the Petrie dish is maintained so that the Petrie dish can be moved along with the microscope table without danger and without extensive optical inspection.

In conventional holder bases, each holder has to be activated separately in order to shift its position. If, for example, it is desired to switch the etching capillary tube from its working position into a resting position, then the corresponding holder must be activated in a suitable way, for example, pneumatically, electrically or in some other way. A separate activation is required once again if, on the return swing, the hollow biopsy needle is supposed to be shifted out of its resting position and into a working position. It is, hence, necessary to have considered precisely beforehand which holder has to be activated and how it has to be activated, especially when several hollow needles are being exchanged between the resting and the working positions. This is a relatively burdensome process for the operator and, especially in the case of lengthy interventions, it can result in undesirable operator errors because of decreased concentration. At a minimum, these operator errors cost time but they also can possibly damage the cellular material.

SUMMARY OF THE INVENTION

An object of the invention is therefore to provide an improved manipulating instrument device to such an extent that it is possible to select and to position the instruments that are needed in each case in a way that is both simpler and safer.

In accordance with this object, the invention provides that drives controlling the holders are so coupled together that when they are activated at least two of the holders are shifted into the working and resting positions, respectively. Consequently, in accordance with the invention the operator can bring about a carefully aimed exchange of positions between the positions of both hollow needles by means of an activation (hence in a single operator step), if during an intervention the above referenced etching capillary tube is located in the working position and the biopsy capillary is in the resting position.

Naturally, the invention is not restricted to a holder base with two holders. It is easily possible for the holder base to make available additional holders. It is also possible that not only two, but additional holders could be shifted into a desired position by means of an activation.

The invention provides for the fact that at least two holders of a holder base are always placed into a desired position in the course of an activation. The concept "to place" has to be interpreted broadly in the context of the invention. It also includes the case in which the holder has been inadvertently left in the position in which the holder should have been placed by being activated. This case may arise, for example, when both holders of a holder base have been lowered into the working position in the context of making adjustments, and then the instrument that initially is not needed in order to make the intervention should be swivelled away out of the working position and into the resting position. Thus, in this case, the holder bearing the etching capillary tube would be "positioned" into the working position in which it was already located, whereas the biopsy capillary actually would be moved into the resting position.

One significant advantage of the invention resides in the fact that from now on it is made certain that after a single activation at least two, and preferably all, instruments contained in a holder base are located in defined positions. This, in consequence, dramatically reduces the number of operator steps required and the likelihood of operator error during a technical cytological intervention.

As discussed above, the working position of the holder constitutes a position in which an instrument can be placed into the field of vision of an observing microscope with its free end. In contrast, the resting position is a position in which it is made sure that the instruments can be positioned in relation to and essentially parallel to the surface of the sample carrier, without thereby running the danger of damaging the cell material that has been placed on the carrier as a result of this arrangement. Such a danger can be especially reliably excluded if the instruments as a whole, when they are in the resting position, are placed above the cellular material. The resting position is preferably chosen so that the free ends of the instruments never leave the oil layer surrounding and covering the samples. In this way, for example, any sucking of air bubbles into the hollow needle is avoided, etc.

The invention provides for at least two of the holders being shifted into one of the two available positions, the resting or the working position, as a result of an activation. The shifting of the two holders may, if desired, be spaced apart in time. However, it is preferable, especially because of the amount of time it saves, if both holders are shifted close to each other in time, that is to say the biopsy hollow needle is being lowered from the resting into the working position while, for example, the etching hollow needle is being moved out of the working position and into the resting position.

As a rule, the holder base designed in accordance with the invention is not placed so as to be permanently attached, for example, to a microscope table (even though this is possible). Rather, it is attached to a control unit that is equipped with a precise drive which makes three-dimensional movement possible. That is to say, the holder base can be positioned with a high degree of precision in all three spatial axes by means of a suitable drive. Such flexibility is required, for example, in conjunction with the macroscopic pre-adjustment, etc.

A further embodiment of the invention in this connection has to do with precision adjustment of the instruments. Precision adjustment is especially necessary because even in the case of the smallest manufacturing tolerances, microscopically detectable deviations can arise between instruments with basically identical dimensions. Consequently, all the instruments mounted in the holders of a holder base must be adjusted before beginning an intervention until their free ends are visible and precisely mapped in the field of vision of the microscope as the respective holders are being engaged in their working position.

One option is to first pre-adjust the holder base and then to lock it into the pre-adjusted position, and to adjust each of its individual holders separately by means, for example, of the set screws provided on them (precision adjustment) until the instruments assume the desired position. This kind of precision adjustment requires the activation, if possible, of several set screws per holder. This can be relatively expensive, however, if there are more than two holders provided in the holder base.

Therefore, a further embodiment of the invention provides that the precision adjustment of the instruments can be accomplished in the working position by means of the control unit to which the holder base is attached and by means of which it can be positioned in the three spatial axes.

For purposes of adjustment, one holder of the holder base is shifted into the working position at a time, for example, and the control unit moves the holder base until the free end of the instrument held by the holder is mapped within the field of vision of the microscope. This value is then stored as a control point in a memory cell and the process is repeated for the next holder of the holder base.

In a preferred embodiment it is provided that the memory cell is coupled with the drives of the holder base in such a way that, when the memory cell is activated to select a desired control point, the entire holder base is moved by means of the precision drive discussed above, and the holder of the holder base for which the specific control point was determined is shifted into the working position. This embodiment has the advantage that an operator can dispense with the time-consuming and expensive adjustment of individual holders by means of adjusting screws, which in addition increases the ease with which he can use the device.

BRIEF DESCRIPTION OF THE DRAWINGS

The invention shall be explained in greater detail hereinafter with reference to the accompanying drawings wherein:

FIG. 2 is a top plan view of the holder base used in the device of FIG. 1.

DESCRIPTION OF THE PREFERRED EMBODIMENTS

Figure 1:
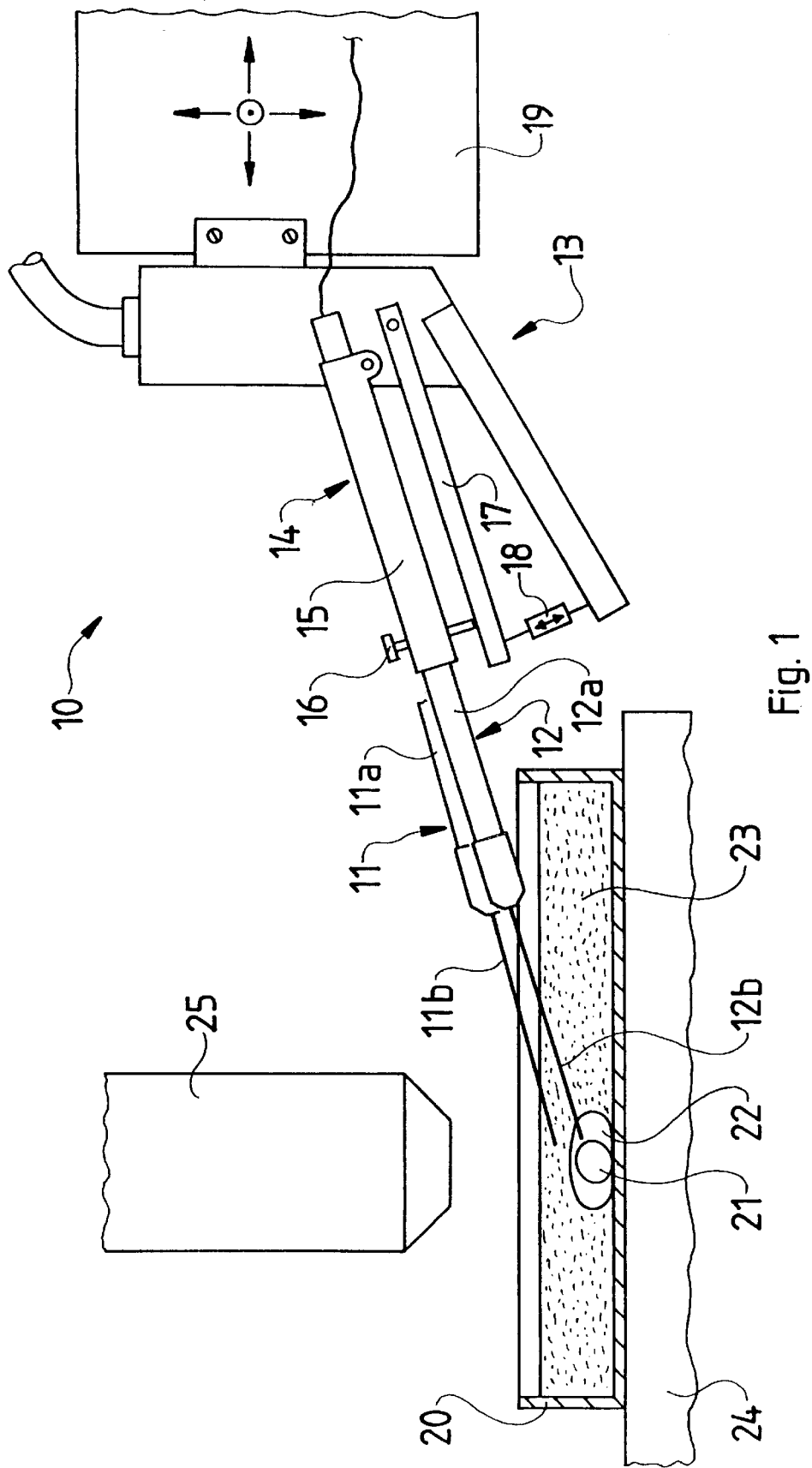
FIG. 1 is a side elevation in section of a device for the handling of instruments used in technical cytological examinations.

FIG. 1 shows a device 10 for handling instruments 11 and 12 used in technical cytological examinations, which instruments consist of hollow needles 11b and 12b, which are mounted in mounting devices 11a and 12a, respectively. Device 10 has a holder base 13 that carries several holders 14, 14' (FIG. 2) for the instruments, of which only holder 14 is shown in FIG. 1. Holder 14 has a bar 15 that holds instrument 12, for example, in a clamping mechanism. One end of clamping bar 15 is mounted in bearings so that it can swing horizontally on holder base 13. The other end of bar 15 runs on bearings supported by a set screw 16 on a flat control element 17 of holder base 13. One end of control element 17 runs on bearings on holder base 13 and can be shifted into either of two different end positions by a drive 18. These end positions correspond to the positions which were previously defined as the working position and the resting position for the holder. In the example shown, the free end of hollow needle 12b of instrument 12 is located in the working position, whereas instrument 11 is mounted in a holder that is not shown in the figure and which had been placed in the rest position. Holder base 13 is attached to a control unit 19 that can move it about three-dimensionally with very great precision by means of a drive mechanism which is preferably a precision drive.

To further elucidate the various positions, FIG. 1 schematically shows a Petrie dish 20 in which has been placed a sample of cellular material 21. Ordinarily, and as shown, sample 21 is enclosed in a drop of culture medium 22 and totally surrounded by a layer of oil 23.

A microscope table 24 on which the Petrie dish 20 rests and a lens 25 of a microscope which is needed for optical inspection of the technical cytological intervention are schematically shown. In the illustrated example, hollow needle 12b of instrument 12 is so positioned by holder 14 that its free end is located as close as possible in direct proximity to cell sample 21 in culture medium 22. In any event, hollow needle 12b of instrument 12 is located in the precisely mapped field of vision of lens 25. Instrument 11, on the other hand, is positioned by the holder which is not shown in the figure into the resting position in which the free end of hollow needle 11b is located at a distance above cell sample 21, but still dipping into the oil pool or film 23. The positions which are illustrated represent ideal positions. Differently selected set-ups are also conceivable, of course, within limits.

As touched upon several times previously, instruments 11 and 12 and the holders containing them have to be adjusted in such a way before beginning an intervention that when, for example, holder 14 is deployed in the working position, the free end of instrument 12 which it contains will be precisely mapped in the field of vision of a microscope lens 25. Holder base 13 is pre-adjusted macroscopically for this purpose, as discussed previously, then each holder 14 of holder base 13 is moved—one after the other—into the working position and positioned by means of precision adjustments until the respective instrument has the desired alignment. The precision adjustment can be accomplished by using the set screw 16 which is shown in the figure. This set screw 16 makes it possible, within limits, to swing clamping bar 15 which contains instrument 11 horizontally relative to support 17, which is moved by control unit 18, whereupon naturally even more set screws or the same sorts of things can be provided for other setting alignments.

The adjustment also can be accomplished using control unit 19, however, to which holder base 13 is attached. To this end, each holder of holder base 13 is once again initially moved into the working position one after the other, then the instrument with its free end is aligned in the desired manner using the control unit 19, and then the position of the control unit is stored in memory as a desired or reference point. This adjustment with subsequent retention in memory is accomplished separately for each holder. During the intervention, the reference positions that are held in memory for the precise instrument that must be used can be called up as needed, whereupon the control unit at first places the holder base into the appropriate position and then the drive unit responsible for lowering the holder in question into its working position is thereafter activated. A device that is exceptionally easy to adjust and to operate is made available in this fashion.

FIG. 2 further illustrates holder base 13 that is being used including mounting devices 11a and 12a that are mounted in clamping bars 15 and 15'. Clamping bars 15 and 15' are linked to holder base 13 and are supported by adjusting screws 16 and 16' located on control elements 17 and 17' which are coupled to drives which are not shown in the figure. This figure serves to complete the illustration of FIG. 1, and it especially provides a better understanding of how the holders are arranged in holder base 13.

This invention is naturally not restricted to the devices shown in the figures. A range of additional embodiments is conceivable. Thus, for example, in the present text instruments are shifted between the resting and the working positions, respectively, by swinging the holder horizontally. But it is also conceivable that the instruments could be shifted in the direction of their longitudinal axis, for instance, or that they could be lifted up as a whole or moved back and forth between positions in some other fashion. The only thing that is important is that the free end of the instruments be visible to the operator in the working position by means of the microscope, and that any damage to the sample of cellular material be excluded when the instrument in the resting position. The drive mechanism for the holders can be made in the most varied ways. Pneumatically operating drives are as conceivable as electric servomotors or even piezoelectric elements. Of course, the invention is not restricted to the capillary tubes and/or precision hollow needles shown in the figures. It is also conceivable, as discussed above, that an operator could manipulate electrodes or other types of tools using a device made in accordance with the invention.

What is claimed is:

1. A device for handling instruments used in technical cytological examination, the device comprising:
    a base;
    at least two separate holders displaceably supported on said base and each carrying an instrument; and
    at least two drives coupled to said at least two holders, respectively, for moving the at least two holders between a working position, in which free ends of respective instruments, which are held in the at least two holders, are aligned during a technical cytological intervention adjacent to a to-be-treated cellular material, and a resting position in which said holders are spaced from the to-be-treated cellular material;
    wherein said at least two drives are coupled with each other so that, when simultaneously actuated, said at least two drives are capable of moving said at least two holders to respective selected positions of said at least two holders, and
    wherein said at least two drives move said at least two holders to the respective selected positions of said at least two holders at equal time intervals or a staggered time intervals.

2. A device according to claim 1 wherein said resting position is located a sufficient distance above said cellular material (21) that said instrument (11) located in a resting position can be moved about freely without contacting said cellular material (21).

3. A device according to claim 1 wherein said holder base (13) is housed in a control unit (19).

4. A device according to claim 3 wherein said control unit (19) comprises a precision drive for moving said holder base (13) three-dimensionally.

5. A device according to claim 4 wherein said precision drive comprises a memory cell for storing retrievable control positions, said cell being coupled with said drives (18) whereby, when the memory cell is activated to select a desired position, said holder base (13) is moved about by said precision drive and at least one of the holders (14, 14') is switched into the working position.

6. A device according to claim 4 wherein said precision drive comprises a memory cell for storing retrievable control positions, said cell being coupled with said drives (18) whereby said holders (14, 14') are selectively both moved into the resting position.

* * * * *